United States Patent
Ladman et al.

(10) Patent No.: US 9,636,519 B2
(45) Date of Patent: May 2, 2017

(54) MAGNETIC STIMULATION METHODS AND DEVICES FOR THERAPEUTIC TREATMENTS

(71) Applicant: BTL HOLDINGS LIMITED, Limassol (CY)

(72) Inventors: Jakub Ladman, Prague-Hlubočepy (CZ); Zdeněk Hurych, Prague-Hlubočepy (CZ); Jiří Mrázek, Prague (CZ); Ondra Prouza, Říčany u Prahy (CZ); Ondrej Pribula, Prague (CZ)

(73) Assignee: BTL Holdings Limited, Limassol (CY)

( * ) Notice: Subject to any disclaimer, the term of this patent is extended or adjusted under 35 U.S.C. 154(b) by 0 days.

(21) Appl. No.: 14/789,658

(22) Filed: Jul. 1, 2015

(65) Prior Publication Data

US 2017/0001027 A1    Jan. 5, 2017

(51) Int. Cl.
  *A61N 2/02*    (2006.01)
(52) U.S. Cl.
  CPC ..................... *A61N 2/02* (2013.01)
(58) Field of Classification Search
  CPC .... A61N 2/006; A61N 2/02; A63B 21/00181; A63B 71/0009; A63B 22/0076; A63B 22/0664; A63B 2220/54; A63B 2213/004
  USPC ....................................... 600/9–15
  See application file for complete search history.

(56) References Cited

U.S. PATENT DOCUMENTS

| | | | |
|---|---|---|---|
| 4,665,898 A | 5/1987 | Costa | |
| 4,993,413 A | 2/1991 | McLeod | |
| 5,085,626 A | 2/1992 | Frey | |
| 5,401,233 A | 3/1995 | Erickson et al. | |
| 5,984,854 A | 11/1999 | Ishikawa et al. | |
| 6,179,769 B1 | 1/2001 | Ishikawa et al. | |
| 6,213,933 B1* | 4/2001 | Lin | A61N 2/02 600/13 |
| 6,402,678 B1 | 6/2002 | Fischell et al. | |
| 6,527,694 B1* | 3/2003 | Ishikawa | A61N 2/02 600/9 |
| 6,939,287 B1 | 9/2005 | Ardizzone et al. | |

(Continued)

FOREIGN PATENT DOCUMENTS

| | | |
|---|---|---|
| EP | 0209246 A1 | 1/1987 |
| EP | 2676700 A2 | 12/2013 |

(Continued)

OTHER PUBLICATIONS

Polk, Charles, "Therapeutic Applications of Low-Frequency Sinusoidal and Pulsed Electric and Magnetic Fields," The Biomedical Engineering Handbook, vol. I, 2000, Second edition, pp. 1625-1636.

(Continued)

*Primary Examiner* — Samuel Gilbert

(74) *Attorney, Agent, or Firm* — Kenneth H. Ohriner; Perkins Coie LLP

(57) ABSTRACT

Methods and devices producing time varying magnetic field have therapeutic uses. The device contains a coil made of insulated wires, an energy storage device, an energy source and a switch. The coil is flexibly attached in a case. The device has at least one blower for cooling the coil. The methods and devices can be used in for example in physiotherapy, neuropsychiatric therapy, aesthetic therapy, urology or urogynecology.

12 Claims, 3 Drawing Sheets

(56) References Cited

U.S. PATENT DOCUMENTS

| | | |
|---|---|---|
| 7,601,115 B2 | 10/2009 | Riehl |
| 7,740,574 B2 | 6/2010 | Pilla et al. |
| 7,744,523 B2 * | 6/2010 | Epstein .......................... 600/9 |
| 7,946,973 B2 | 5/2011 | Peterchev |
| 7,998,053 B2 * | 8/2011 | Aho .................... A61N 2/02 336/210 |
| 9,002,477 B2 | 4/2015 | Burnett |
| 2001/0031906 A1 | 10/2001 | Ishikawa et al. |
| 2006/0152301 A1 | 7/2006 | Rohwedder |
| 2006/0187607 A1 | 8/2006 | Mo |
| 2008/0262287 A1 | 10/2008 | Dussau |
| 2010/0087699 A1 | 4/2010 | Peterchev |
| 2010/0331603 A1 | 12/2010 | Szecsi |
| 2011/0021863 A1 | 1/2011 | Burnett |
| 2012/0053449 A1 | 3/2012 | Moses |
| 2013/0158634 A1 | 6/2013 | Edoute |
| 2013/0238061 A1 | 9/2013 | Edoute |
| 2013/0317281 A1 | 11/2013 | Schneider |
| 2014/0046423 A1 | 2/2014 | Rajguru |
| 2015/0025299 A1 | 1/2015 | Edoute |
| 2015/0157873 A1 | 6/2015 | Sokolowski |
| 2015/0367141 A1 | 12/2015 | Goetz |
| 2016/0051827 A1 | 2/2016 | Edoute |

FOREIGN PATENT DOCUMENTS

| | | |
|---|---|---|
| WO | 02/25675 A1 | 3/2002 |
| WO | 03/090863 A1 | 11/2003 |

OTHER PUBLICATIONS

Heisel, Jürgen, Physikalische Medizin. Stuttgart: Georg Thieme Verlag KG, 2005. ISBN 3-13-139881-7. p. 159.

Yasuhiro Izumiya et al., "Fast/Glycolytic Muscle Fiber Growth Reduces Fat Mass and Improves Metabolic Parameters in Obese Mice", Cell Metab. Feb. 2008; 7(2): 159-172.

Vernon W.H. Lin et al., "Functional Magnetic Stimulation: A New Modality for Enhancing Systemic Fibrinolysis", Arch Phys Med Rehabil vol. 80, May 1999, pp. 545-550.

* cited by examiner

MAGNETIC STIMULATION METHODS AND DEVICES FOR THERAPEUTIC TREATMENTS

BACKGROUND OF THE INVENTION

Devices and methods generating magnetic pulses have long been used for medical treatments. A time-varying magnetic field induces electric currents in the patient's body, which may provide similar effect as electrotherapeutic treatment. With sufficient intensity, duration and repetition rate, the induced electrical currents may evoke action potential of neurons, muscle fibers and endocrine cells. The advantage of the methods using magnetic field compared with electrotherapeutical methods is that changing magnetic field therapy does not require contact with the patient and can be performed through clothing. With magnetic field treatments, the stimulating signal does not pass through the skin. Rather, the electrical currents are induced directly in the stimulated tissue. This increases stimulation focus and eliminates unwanted side effects of the therapy (e.g. skin irritation). Using a sufficiently large magnetic flux density and/or repetition rate, it is possible to stimulate various tissues without need of invasive methods.

SUMMARY OF THE INVENTION

A time varying magnetic field may be used to treat variety disorders and injuries of muscle, nerve and connective tissue. It may also be used also in physiotherapy, aesthetic therapy, urology, urogynecology, psychiatry, neurology and neurophysiology for therapy and diagnosis/prognosis.

A device for time variable magnetic field generation may include an energy source, an energy storage device, a switching circuit, a coil and possibly a core. The energy storage device accumulates tens of Joules of energy and the magnetic flux density induced by the coil is in the range of tenths of a Tesla to about one Tesla.

Existing devices have low efficiency and they waste energy, which limits their use. Eddy currents induced within the coil create engineering challenges. Existing devices contain coils which are made of metallic strips, electric wires or hollow conductors. Since the therapy requires large currents, significant losses are caused by induced eddy currents within the coil. Eddy currents lead to production of unwanted heat and therefore there is need to sufficiently cool the coil. Also, the energy source must be protected during reverse polarity of resonance. This requires using protective circuits which consume significant amounts of energy.

Due to low efficiency, existing devices may not achieve repetition rates of magnetic pulses above one hundred Hertz, as may be needed to produce a magnetic flux density sufficient for acting on neurons, muscle fibers and/or endocrine cells (e.g. at least partial muscle contraction). Using existing devices, interruptions during therapy or between therapies are often necessary to avoid overheating the device.

The present methods and devices as described below produce a time varying magnetic field for patient treatment which better optimizes energy use, increases the effectiveness of the treatments and provide a new treatment. The magnetic pulses may be generated in monophasic, biphasic or polyphasic regimes. In a first aspect, the device has one or more coils; a switch; an energy storage device and a connection to an energy source. The coil may be made of insulated wires with a conductor diameter less than 3 mm even more preferably less than 0.5 mm and most preferably less than 0.05 mm. Smaller diameter and individual insulation of the wires significantly reduces self-heating of the coil and therefore increase efficiency of magnetic stimulation device. The coil may be flexibly attached in a casing of device. The casing may comprise a blower or blowers which ensure cooling of the coil.

Space between the insulated wires may be filled with a solid material so as to reduce the noise caused by vibrations. The coil is connected with an energy storage device which serves as a storage of energy.

The switch can be any kind of switch such as diode, MOSFET, JFET, IGBT, BJT, thyristor or a combination of them. The switch can be connected in parallel to the coil and the energy storage device, to eliminate reversal polarity of high voltage on the terminals of the energy source in the second half of the resonant effect. Therefore there is no need for additional protective circuits to protect the energy source from the negative voltage. Electric losses associated with such protective circuits are avoided. Energy use is reduced. The voltage drop in the energy storage device between first and second oscillation maximum during resonance is also reduced. Via the lower voltage drop, higher repetition rates of magnetic pulses and higher magnetic flux density may be achieved for treatment of the patient.

The coil of the magnetic stimulation device may be flexibly attached to casing of the device. The blower or blowers may be arranged to blow air on both sides of coil. Optionally, the coil may be a flat type coil.

As used here "continual therapy" and "continual magnetic stimulation" means therapy where the set of the magnetic flux density and frequency/repetition rate of magnetic pulses does not lead to exceeding of the operating temperature 43° C. on the casing of the device operating in an ambient temperature of 30° C. regardless of the duration of therapy.

DETAILED DESCRIPTION

Figure 1:
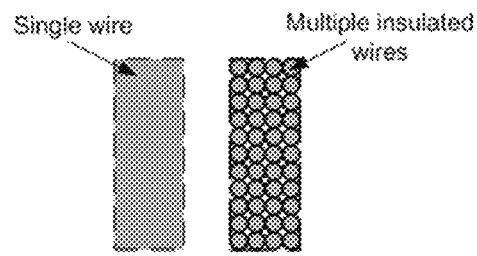
FIG. 1 is a cross section view of a coil winding.

FIG. 1 illustrates a cross section of winding of a coil for a magnetic stimulation device. The coil may be constructed from litz-wire, wherein each wire is insulated separately. Each individual conductor is coated with non-conductive material so the coil constitutes multiple insulated wires. Unlike existing magnetic coil conductors, the present coil is not made of bare wire e.g. litz-wire without insulation, or conductive tapes, conductive strips, or copper pipe with hollow inductors. The insulation of wires separately is a substantial improvement, since this leads to a significant reduction of the induced eddy currents. Power loss due to eddy currents, per single wire, is described by Equation 1 below. The small diameter wires of the present coil significantly reduce self-heating of the coil and therefore increases efficiency of the present magnetic stimulation device:

$$P_{EDDY} = \frac{\pi^2 \cdot B_P^2 \cdot d^2 \cdot f^2}{6 \cdot k \cdot \rho \cdot D}, \qquad \text{Eq. 1}$$

where: $P_{EDDY}$ is power loss per unit mass (W·kg$^{-1}$); $B_p$ is the peak of magnetic field (T); f is frequency (Hz); d is the thickness of the sheet or diameter of the wire (m); k is constant equal to 1 for a thin sheet and 2 for a thin wire; ρ is the resistivity of material (Ω·m); D is the density of material (kg·m$^3$).

The individual insulation of each wire reduces eddy currents. The individually insulated wires may be wound either one by one or in a bundle of individually insulated wires so as to form a coil, which will serve as a magnetic field generator. The coil provides an improvement in the efficiency of energy transfer in the LC resonant circuit and also reduces or eliminates unwanted thermal effects.

The coil may have a planar coil shape where the individually insulated wires may have cross-section wires with conductor diameter less than 3 mm even more preferably less than 0.5 mm and most preferably less than 0.05 mm. The wires are preferably made of materials with higher density and higher resistivity e.g. gold, platinum or copper. The diameters of the single wires should be minimal. On the other hand the total diameter should be maximal because of inverse proportion between the cross-section of all wires forming the coil and the electrical resistance. Therefore the ohmic part of the heat is then lower. Eq. 2 describes power loss of the coil:

$$P_R = \frac{\rho \cdot \frac{l}{S} \cdot I^2}{m} \quad \text{Eq. 2}$$

Where: $P_R$ is the power loss heat dissipation (W); ρ is the resistance (Ω·m); l is the length of wire (m); S is the surface area (m$^2$); l is the current (A) and m is 1 kg of wire material.

Total power loss is (Eq.3):

$$P_{TOT} = P_{EDDY} + P_R, \quad \text{Eq. 3}$$

Where: $P_{TOT}$ is the total power losses (W·kg$^{-1}$); $P_{EDDY}$ is the power dissipation of eddy currents (W·kg$^{-1}$); $P_R$ is the power loss heat dissipation (W·kg$^{-1}$).

Dynamic forces produced by current pulses passing through the wires of the coil cause vibrations and unwanted noise. The individual insulated wires of the coil may be impregnated under pressure so as to eliminate air bubbles between the individual insulated wires. The space between wires can be filled with suitable material which causes unification, preservation and electric insulation of the system. Suitable rigid impregnation materials like resin, and elastic materials like PTE can be also used. With the coil provided as a solid mass, the vibrations and resonance caused by movements of the individual insulated wires are suppressed. Therefore noise is reduced.

The coil may be attached to the case of the applicator, such as a hand held applicator of the magnetic stimulation device; built-in applicator in e.g. chair, bed; or stand-alone applicator e.g. on mechanical fixture. The attachment may be provided by an elastic material e.g., silicone, gum; or other flexible manner. Connection with the coil of the applicator's case can be ensured by several points. The several fastening points ensure the connection of the coil to the casing by flexible material so that the main part of the coil and the main part of the casing of applicator are spaced apart. The spacing should be at least 0.1 mm so that air can easily flow. The gap between the coil and the casing can be used either for spontaneous or controlled cooling. The coil may optionally be connected to the case of the applicator by only one fastening point. The fastening points eliminate vibrations of wires which could be transferred to housing of the applicator and therefore reduce noise of the magnetic stimulation device.

Figure 2:
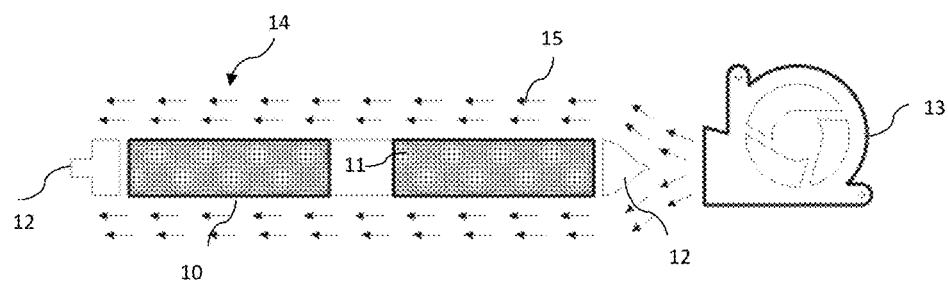
FIG. 2 is an illustrative embodiment of cross-section of the magnetic applicator.

FIG. 2 is a cross-section of the magnetic applicator which allows better flow on the lower and upper sides of the coil and thus more efficient heat dissipation. The magnetic stimulation device includes a coil 10, the circuit wires 11 and the fastening points 12 for connection of the coil to the casing of the applicator (not shown). The fastening points 12 are preferably made of flexible material however the rigid material may be used as well. The fastening points 12 may be located on the outer circumferential side of the coil. However, alternatively it is possible to put these fastening points to a lower or upper side of the coil.

The fastening points 12 connect the coil to the case of the applicator in at least one point. The fastening points 12 maintain the coil and the main part of the case of the applicator spaced apart so that fluid (which may be air or any liquid) can flow between them. At least one blower 13 can be placed around the circumference of the coil, or perpendicular to the coil. The blower can be any known kind of device for directing the fluid e.g. outer air directed into the case of the applicator. This arrangement of the blower allows air to bypass the coil from upper and lower (patient's) sides. In still another embodiment the outer air can be cooled before directing into the case. The blower can have an inlet placed around the circumference of the coil for injecting air, to remove heat from the coil. A connecting tube (not shown) can ensure connection of the applicator 14 with the energy source and/or control unit of magnetic stimulation device. The connecting tube may also contain a conduit of the fluid.

The arrows 15 indicate the air flow through the applicator 14. This arrangement of the blower allows the air to bypass the coil from upper and lower (patient's) side. Outlet may be preferably placed on upper side of the casing. By placing the blower around the circumference of the coil instead of on the top/below the coil, the blower 13 does not interfere with the magnetic flux peak and therefore its lifespan and reliability is increased.

Figure 3:
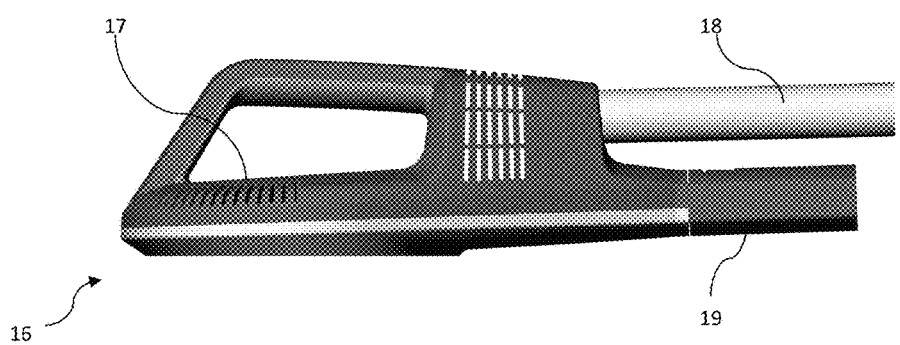
FIG. 3 is an illustrative embodiment of a casing of the magnetic applicator.

FIG. 3 is an illustrative embodiment of a casing of the magnetic applicator. The overview drawing contains casing itself 16, which might contain an outlet 17 preferably placed on upper side of the casing 16. A connecting tube 18 may not only ensure connection of the applicator with the energy source and/or control unit of magnetic stimulation device, but also connection to a source of the fluid; however the conduit of the fluid 19 may also be connected separately.

Figure 4A:
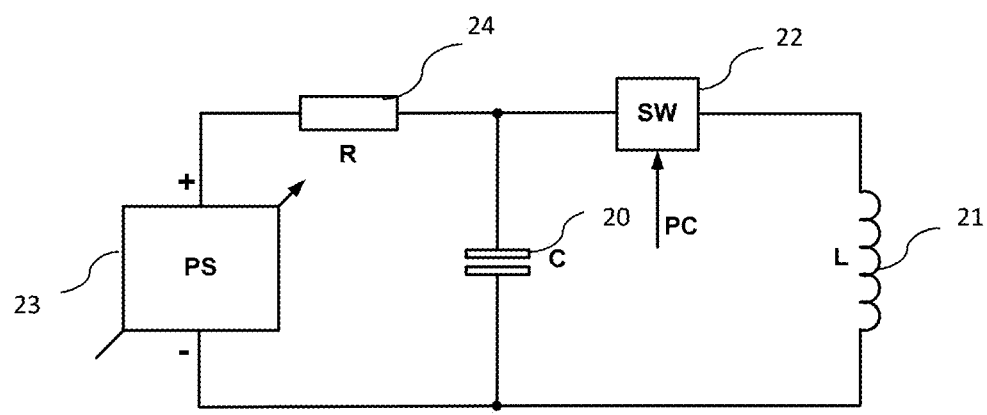
FIGS. 4A and 4B illustrates circuit for providing high power pulses to a stimulating coil.
Figure 4B:
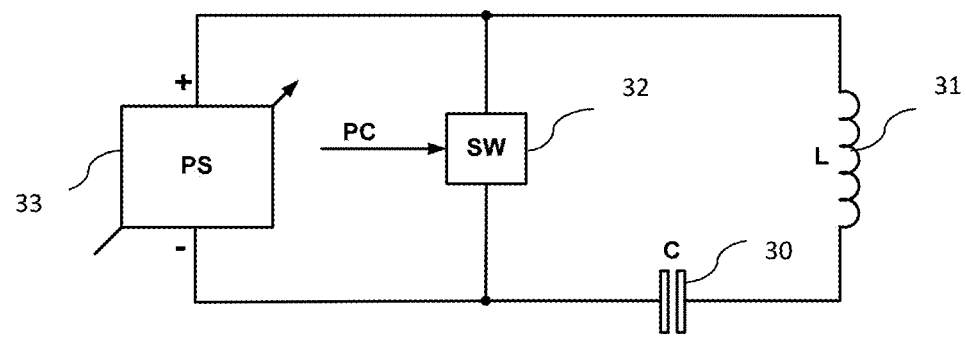

FIG. 4A and FIG. 4B illustrate circuits for providing high power pulses to the stimulating coil. FIG. 4A shows a circuit for providing high power magnetic pulses. FIG. 4B shows a circuit for providing high power pulses.

Existing magnetic stimulation devices achieve magnetic flux density of a few tenths to several Teslas. To achieve this level of magnetic flux density, the energy source used generates sufficient voltage. This voltage can reach thousands of volts. In FIG. 4A the circuits for providing high power pulses to the stimulating coil contain a series connection to the switch 22 and the coil 21. The switch 22 and the coil 21 together are connected in parallel with an energy storage device 20. The energy storage device 20 is charged by the energy source 23 and the energy storage device 20 then discharges through the switching device 22 to the coil 21.

During second half-period of LC resonance, the polarity on the energy storage device 20 is reversed in comparison with the energy source 23. In this second half-period, there is a conflict between energy source 23, where voltage on positive and negative terminals is typically thousands of Volts. The energy storage device 20 is also charged to the positive and negative voltage generally to thousands of Volts. As a result, there is in the circuit, consequently, twice the voltage of the energy source 23. Hence the energy source 23 and all parts connected in the circuit are designed for a high voltage load. Therefore, the protective resistors and/or protection circuitry 24 must be placed between energy source 23 and energy storage device 20. As a result a large amount of energy is transformed to undesired heat in the protective resistors and/or protection circuitry 24.

FIG. 4B shows a circuit for providing high power pulses for improved function of the magnet stimulation device. The coil 31 and an energy storage device 30 are connected in series and disposed in parallel to the switch 32. The energy storage device 30 is charged through the coil 31. To provide an energy pulse, controlled shorting of energy source 33 takes place through the switch 32. In this way the high voltage load at the terminals of the energy source 33 during the second half-period of LC resonance associated with known devices is avoided. The voltage on the terminals of energy source 33 during second half-period of LC resonance is a voltage equal to the voltage drop on the switch 32.

The switch 32 can be any kind of switch such as diode, MOSFET, JFET, IGBT, BJT, thyristor or their combination. Depending on the type of component the load of energy source 33 is reduced to a few Volts, e.g., 1-10 volts. Consequently, it is not necessary to protect the energy source 33 from a high voltage load, e.g., thousands of Volts. The use of protective resistors and/or protection circuits is reduced or eliminated. The present designs simplify the circuits used, increase efficiency of energy usage and provide higher safety.

Figure 5:
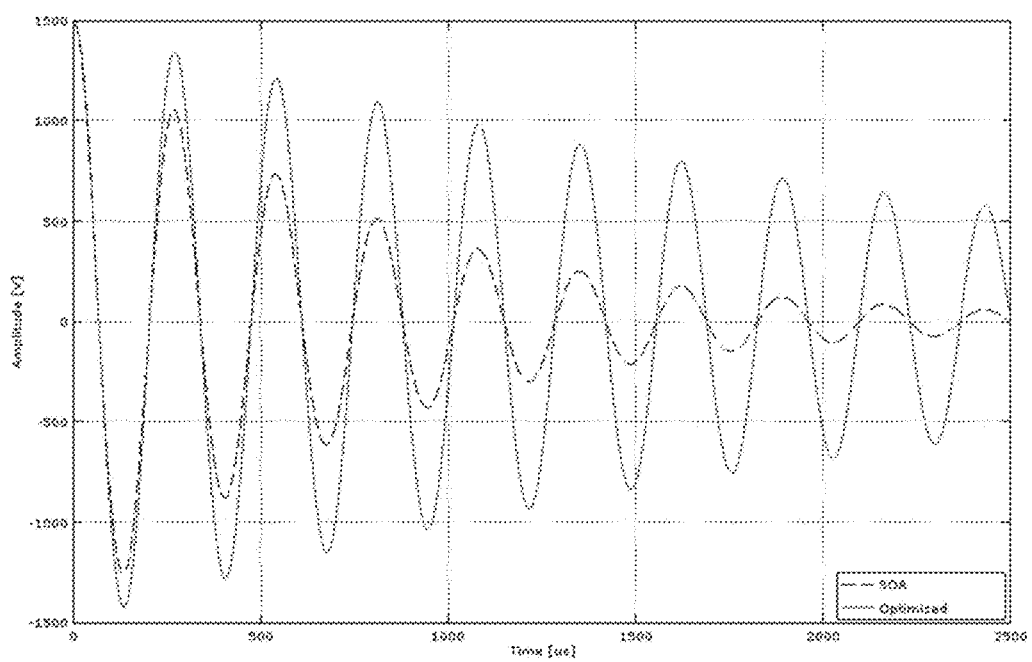
FIG. 5 is a graph showing voltage drop in the energy storage device.

FIG. 5 show an exponential voltage drop in the energy storage device. Energy savings during time-varying magnetic therapy may be characterized by reduced voltage drop in the energy storage device between the first, second and subsequent maximums of the resonant oscillation. The magnitude of the individual voltage oscillations is exponentially dampened up to establishing the energy balance. This allows increasing the maximum possible frequency/repetition rate of magnetic pulses, since the frequency/repetition rate is dependent on the speed with which it is possible to recharge the energy storage device. Since the energy storage device is recharged by the amount of energy loss during the previous pulse, it is possible to increase the frequency/repetition rate of the device up to hundreds of magnetic pulses per second without the need to increase the input power. The voltage drop between any of the successive amplitudes is not higher than 21%, even more preferably not higher than 14% and most preferably not higher than 7%.

The device can be used for treatment/successive treatments in continual, interrupted or various duty cycle regime. The duty cycle may be higher than 10%, which means interrupted regime with the ratio up to 1 active to 9 passive time units. The ratio may possibly change during the therapy. The device enables operation defined by the peak to peak magnetic flux density on the coil surface at least 3 T, more preferably at least 2.25 T, most preferably at least 1.5 T at repetition rates above 50 Hz, more preferably at repetition rates above 60 Hz, even more preferably at repetition rates above 70, most preferably at repetition rates above 80 Hz with treatment/successive treatments lasting several seconds or longer, for example, for at least 5, 10, 30, 60, 120 or 240 seconds, or longer. The total power consumption is below 1.3 kW and the width of pulses is in the range of hundreds of μs.

The device enables achieving repetition rates above 100 Hz, more preferably repetition rates above 150 Hz, most preferably repetition rates above 200 Hz with the magnetic flux density providing a therapeutic effect on neurons and/or muscle fibers and/or endocrine cells (e.g. at least partial muscle contraction, action potential in cell). Based on achievement of repetition rates in order of few hundreds the device also enables assembling the magnetic pulses into the various shapes (e.g. triangular, rectangular, exponential), with the shape widths from 6 ms to several seconds or longer.

Thus, novel devices and methods have been shown and described. Various changes and substitutions may be made without departing from the spirit and scope of the invention. The invention, therefore, should not be limited except to the following claims and their equivalents.

The invention claimed is:

1. A magnetic stimulation device producing a time varying magnetic field for treatment, comprising:
    a connection to an energy source, a switch, a coil, an energy storage device, at least one blower and a casing;
    with the blower arranged on a circumference of the coil; and
    wherein the coil and the casing are arranged in a manner that fluid can flow in-between them and wherein the coil is cooled by fluid flow over at least upper and lower sides of the coil.

2. The device of claim 1 wherein the fluid is air.

3. The device of claim 2 wherein the coil is a flat type coil.

4. The device of claim 2 wherein the coil comprises insulated wires.

5. The device of claim 2 wherein the coil is attached to the casing by at least one fastening point.

6. The device of claim 5 wherein the at least one fastening point is located on an outer circumferential side of the coil to enable fluid flow over at least the upper side and the lower side of the coil.

7. The device of claim 6 wherein the at least one fastening point is flexible.

8. The device of claim 6 comprising a plurality of fastening points and wherein at least one of the fastening points is rigid.

9. The device of claim 5 wherein the at least one fastening point is rigid.

10. The device of claim 1 wherein a spacing for fluid flow of at least 0.1 mm is provided between the upper and/or the lower side of the coil and the casing.

11. The device of claim 1 further including an outlet on an upper side of the casing.

12. A magnetic stimulation device producing a time varying magnetic field, comprising:
    an energy source electrically connected to a switch, a flat coil, and an energy storage device;
    at least one blower in a casing, with the blower on one side of the coil and positioned to blow air across upper and lower sides of the flat coil, in a direction parallel to the upper and lower sides of the flat coil; and
    with at least one of the upper and lower sides of the flat coil spaced apart from the casing to allow air to flow between them, to cool the coil.

* * * * *